United States Patent [19]

Degobert et al.

[11] Patent Number: 4,594,968
[45] Date of Patent: Jun. 17, 1986

[54] PROCESS AND DEVICE FOR DETERMINING THE COMPOSITION OF AN ALCOHOL-PETROL MIXTURE, ADAPTED TO THE AUTOMATIC REGULATION OF ENGINES FED WITH FUEL MIXTURES HAVING A VARIABLE ALCOHOL CONTENT

[75] Inventors: Paul Degobert, Rueil Malmaison; Michel Mauté, Les Clayes Sous/Bois; Gerald Banet, Rueil Malmaison, all of France

[73] Assignee: Institut Francais du Petrole, France

[21] Appl. No.: 586,278

[22] Filed: Mar. 5, 1984

[30] Foreign Application Priority Data

Mar. 3, 1983 [FR] France .................................. 83 03663

[51] Int. Cl.$^4$ ........................... F02B 75/12; G01J 1/00
[52] U.S. Cl. .................... 123/1 A; 123/494; 123/575; 250/343
[58] Field of Search ............... 123/1 A, 478, 575, 576, 123/577, 578, 494; 250/338, 343, 344, 345; 356/73

[56] References Cited

U.S. PATENT DOCUMENTS

| 3,562,524 | 2/1971 | Moore et al. | 250/343 |
| 3,792,272 | 2/1974 | Harte et al. | 250/343 |
| 4,306,152 | 12/1981 | Ross et al. | 250/345 X |
| 4,329,048 | 5/1982 | Capitini et al. | 356/73 |
| 4,369,736 | 1/1983 | Ito | 123/575 X |
| 4,371,785 | 2/1983 | Pedersen | 250/345 X |
| 4,391,253 | 7/1983 | Ito | 123/480 X |
| 4,438,749 | 3/1984 | Schwippert | 123/494 |

Primary Examiner—Tony M. Argenbright
Attorney, Agent, or Firm—Antonelli, Terry & Wands

[57] ABSTRACT

A process and device for determining the composition of an alcohol-petrol mixture supplying a combustion engine. According to this process a light beam is emitted through the mixture supplying the engine, the degree to which this beam is absorbed by the mixture is determined in a wave length chosen in the wave length range corresponding to the near infra-red and adjustment of the operating parameters of the engine is controlled as a function of the degree of absorption thus measured.

13 Claims, 6 Drawing Figures

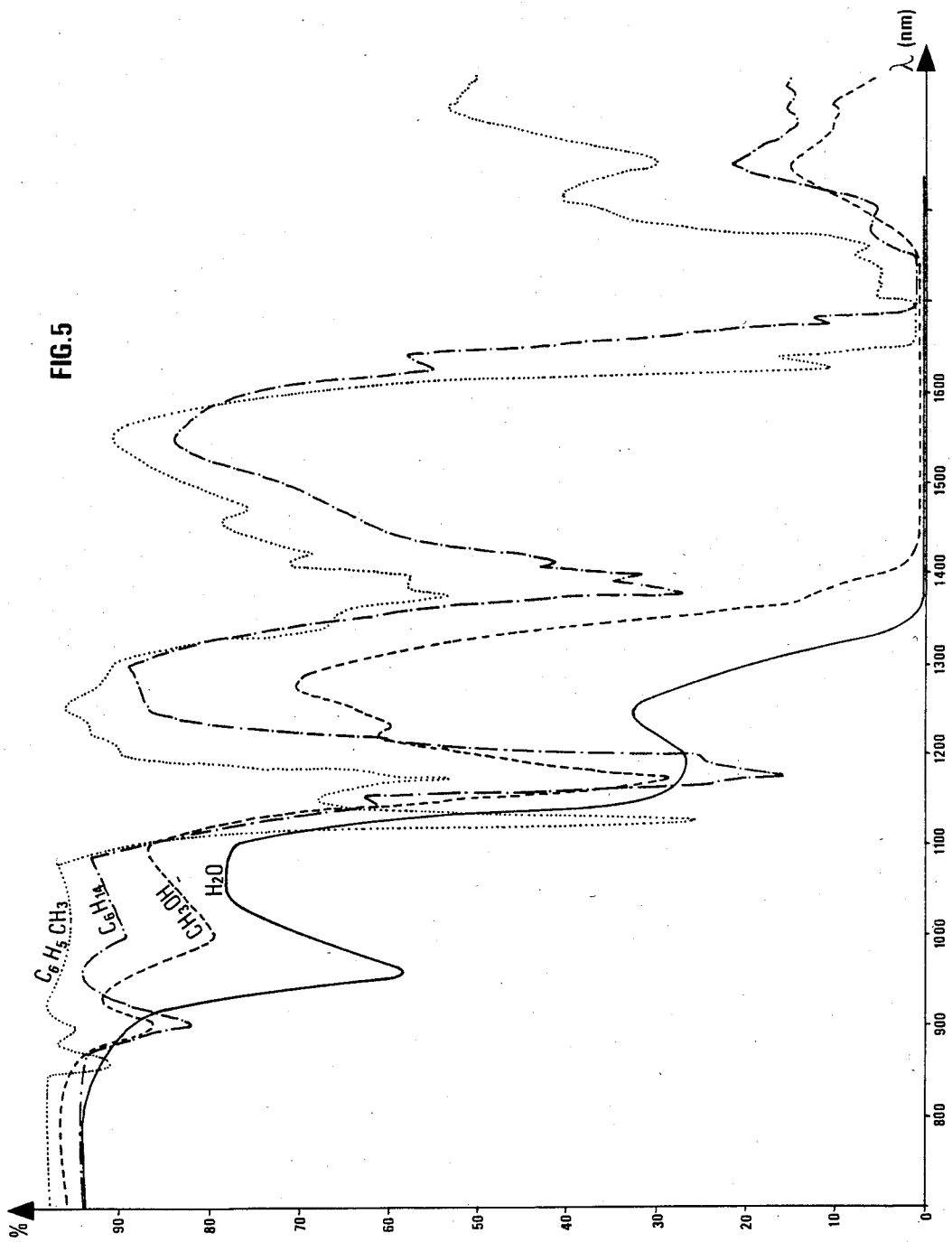

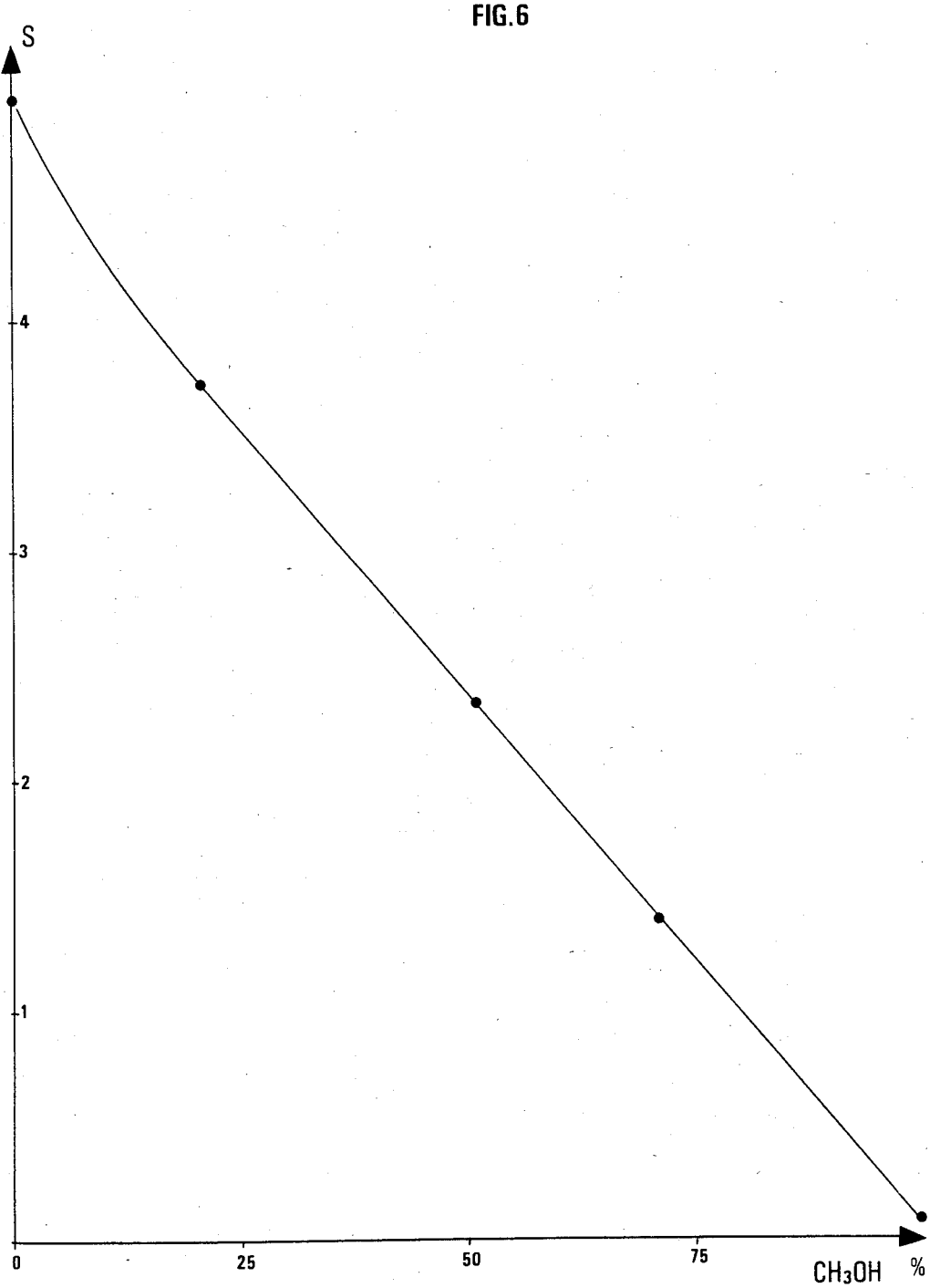

PROCESS AND DEVICE FOR DETERMINING THE COMPOSITION OF AN ALCOHOL-PETROL MIXTURE, ADAPTED TO THE AUTOMATIC REGULATION OF ENGINES FED WITH FUEL MIXTURES HAVING A VARIABLE ALCOHOL CONTENT

BACKGROUND OF THE INVENTION

1. Field of the Invention

The present invention relates to a process and device for determining the composition of an alcohol-petrol mixture, adapted to the automatic regulation of engines fed with fuel mixtures having a variable alcohol content.

In order to use the different types of fuels which will be commercially available in the future, flexible engines using polyfuels will have to have an integrated system for adapting to the different fuels, or to the mixtures of the different fuel formulations, on the one hand, and for automatically adjusting the fuel/air ratio and the ignition, on the other hand.

The essential object of the present invention is to satisfy these different requirements.

To resolve the problem thus posed, the invention provides a process for determining the composition of an alcohol-petrol mixture, in which a light beam is emitted through the mixture and the degree to which this beam is absorbed by the mixture is determined for at least one wave length chosen in the wave length range corresponding to the near infra-red, this degree of absorption being related to the alcohol content of the mixture.

By "near infra-red" is to be understood the zone of the light spectrum corresponding to a wave length between 0.7 and 1.7 micro (700 to 1700 nanometers).

2. Description of the Prior Art

French Pat. No. 2,487,010 and the article entitled "Probleemloze toepassing van alcoholbenzine-mengsels in auto's" published in March 1981 on pages 117–122 of number 3 (volume 36) of the revue "Polytechnisch Tijdschrift Werktuigbouw" describe a device for measuring the percentage of alcohol in the fuel. This device uses light transmission in a glass column, but it does not define the light absorbed by the fuel in the near infrared. More generally, it is not known in the Prior Art to use the absorption of light in the near infra-red by an alcohol-petrol mixture for determining the composition of this mixture.

The Prior Art may be illustrated by the U.S. Pat. Nos. 4,369,736, 3,996,785, 4,031,864 and 4,321,465 and British Pat. No. 1,554,309.

SUMMARY OF THE INVENTION

More particularly, the invention provides a process for automatically adjusting the operating parameters of a combustion engine fed with an alcohol-petrol mixtures, wherein a light beam is emitted through the mixture supplying the engine, the degree to which this beam is absorbed by the mixture is determined in a wave length band chosen in the wave length range corresponding to the near infra-red and the adjustment of the operating parameters of the engine is provided as a function of the degree of absorption thus measured.

In a first embodiment of the invention, the degree of absorption is determined for a wave length between 900 and 1000 nanometers (1 nanometers = $10^{-9}$ meter).

In a second embodiment of the invention, the degree of absorption is determined for a wave length between 1,450 and 1,600 nanometers.

Still within the scope of the present invention, the degree to which said first beam is absorbed by the mixture may be compared with the degree to which a second beam, possibly having the same source as the first beam, is absorbed by a reference fluid such as pure alcohol, or an alcohol-petrol mixture of known composition.

The invention also provides a device useable for the automatic adjustment of at least one operating parameter of a combustion unit such as an engine, fed with an alcohol-petrol mixture, such as the air/fuel ratio of the supply, the ignition advance, or the recycling rate of the unburnt gases, which device comprises a sensor having a light source which emits a light beam through a cell through which flows the fuel mixture supplying the engine, and a means for measuring the degree to which this beam is absorbed by the mixture flowing through the cell for at least one wave length chosen in the wave length range corresponding to the near infra-red, this measurement means delivering a signal depending on the measured degree of absorption.

The invention relates more especially to a device such as defined above, wherein said measuring means is connected to means for adjusting at least one operating parameter of an engine as a function of said signal delivered by said measuring means.

In a particular embodiment, this device is characterized in that said sensor is disposed in series with a fuel pump in the supply pipe connecting the fuel reservoir to the engine, in that the reservoir comprises a fuel gauge adapted to produce a signal translating an increase in the volume of fuel in the reservoir, and in that a by-pass duct to the return pipe to the reservoir is disposed in the supply pipe and connected to the means for controlling the by-pass, these control means being adapted for activation during a given time interval, on receiving a control signal delivered by the gauge and related to an increase in the volume of fuel in the reservoir.

BRIEF DESCRIPTION OF THE DRAWINGS

The invention is illustrated by the accompanying drawings in which:

FIG. 5 shows the percentage of light transmission for different components of fuel mixtures, as a function of the wave length; and FIG. 6 shows one example of a calibration curve of a measuring means such as those shown in FIG. 3.

The accompanying drawings illustrate one embodiment of the invention.

DESCRIPTION OF THE PREFERRED EMBODIMENT

Figure 1:
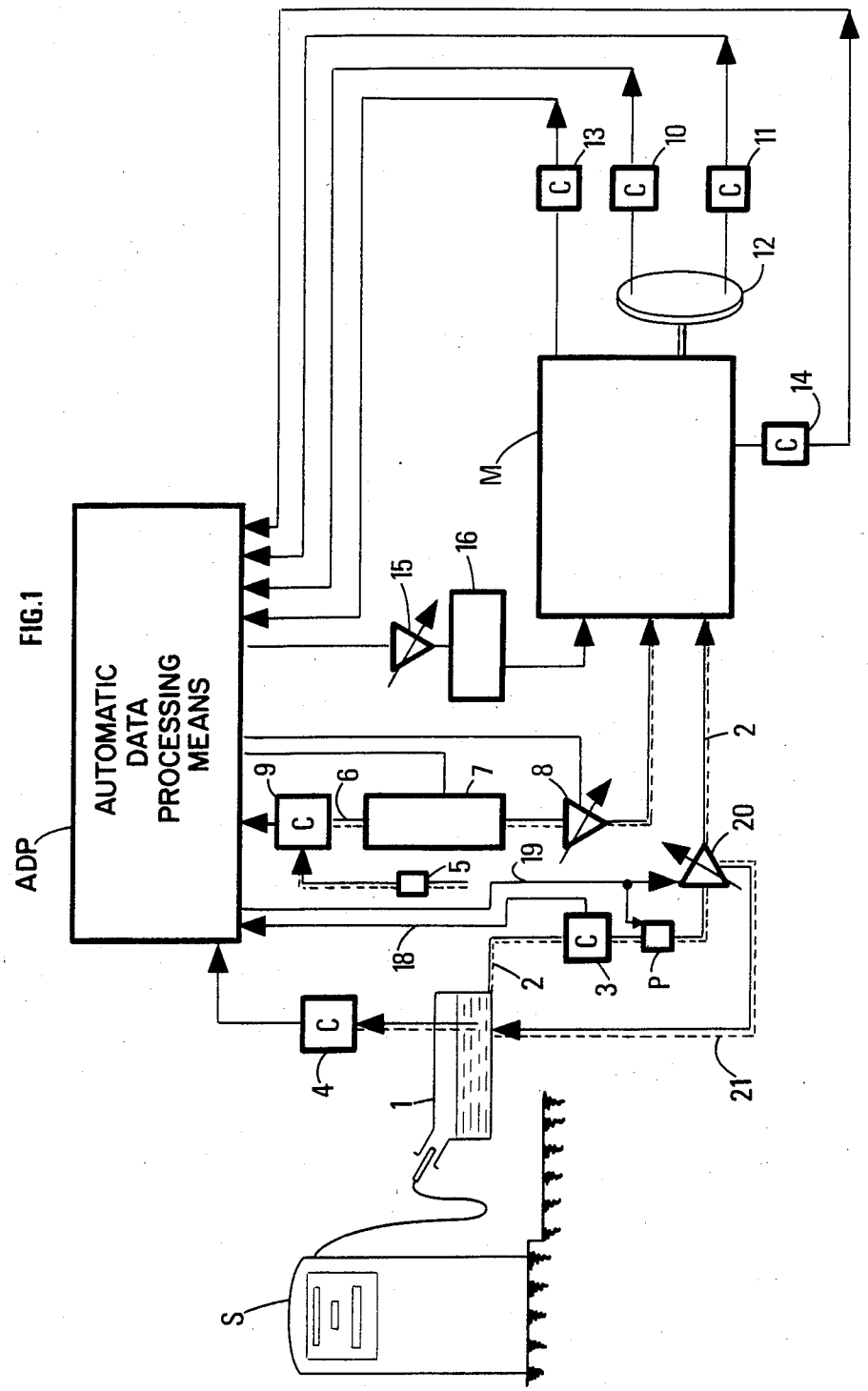
FIG. 1 is a simplified general view of a device in accordance with the invention adapted for automatically adjusting the operation of an internal combustion engine.

In FIG. 1, illustrating schematically one embodiment of the invention, reference M designates an engine supplied with fuel from reservoir 1 through pipe 2, in which is placed the petrol pump P and the device 3 for determining the alcohol content of the fuel. The level of fuel is reservoir 1 is measured by gauge 4. The air supply is provided through the air filter 5 and a pipe 6 passing through a heater 7 and in which is placed an electro magnetic valve 8 for adjusting the air supply. This supply is measured by sensor 9. Other sensors 10 and 11, cooperating with a fly wheel 12 rotated by the engine, determine, respectively, the rotational speed of the engine and the passage of the piston through top dead center in each cylinder for each engine cycle.

A combustion sensor 13 determines the abnormal combustion cycles when the pinging or knocking phenomenon appears.

A probe 14 placed in the exhaust gases determines whether these gases come from the combustion of a stoichiometric fuel-air mixture.

The indications from the different sensors mentioned above and schematized by the letter C in the drawings are transmitted to an automatic data processing means ADP, of the micro-processor type which delivers adjustment signals to the electro magnetic valve 8 and to a means 15 for controlling the ignition circuit 16 of the engine.

The automatic data processing means ADP may be adapted for automatically adjusting the ignition advance to an optimum value avoiding the appearance of pinging, as a function of the signals received, in particular, from sensors 10, 11 and 13, for example in accordance with the process described in U.S. Pat. No. 4,120,272.

Sensor 3 measuring the percentage of alcohol in the fuel transmits its measuring signal to the automatic data processing means ADP through the conductor 18.

This measurement may be made continuously or discontinuously.

In this latter case, the last measurement made is stored by the automatic data processing means ADP, a new measurement being made after each refilling of reservoir 1.

For this, gauge 4 may be adapted to deliver a signal to control means associated with the automatic data processing means ADP at each increase of the fuel level in reservoir 1.

The processor then actuates, through conductor 19, a three-way electromagnetic valve 20, placed in the feed pipe 2 of the output of pump P, this electromagnetic valve opening a by-pass 21 connected to reservoir 1, so as to cause the fuel to flow in a closed circuit, through pipe 2 and return pipe 21 to the reservoir, for a given period of time of, for example 1 to 2 minutes defined by the automatic data processing means ADP.

This operation allows homogenization of the fuel compositions in reservoir 1 and in the pipe to be obtained and, at the end of the fixed period of time, the automatic data processing means ADP transmits to the electromagnetic valve 20 a signal causing the by-pass to the return pipe 21 to the reservoir to be closed for supplying the engine with fuel.

The measurement of the alcohol content effected by sensor 3 and transmitted through conductor 18 is then recorded by the automatic data processing means ADP, where it replaces the value previously stored by this latter, after the preceding replenishment of reservoir 1 with fuel.

It would also be possible to dispose sensor 3 in pipe 21.

Figure 2:
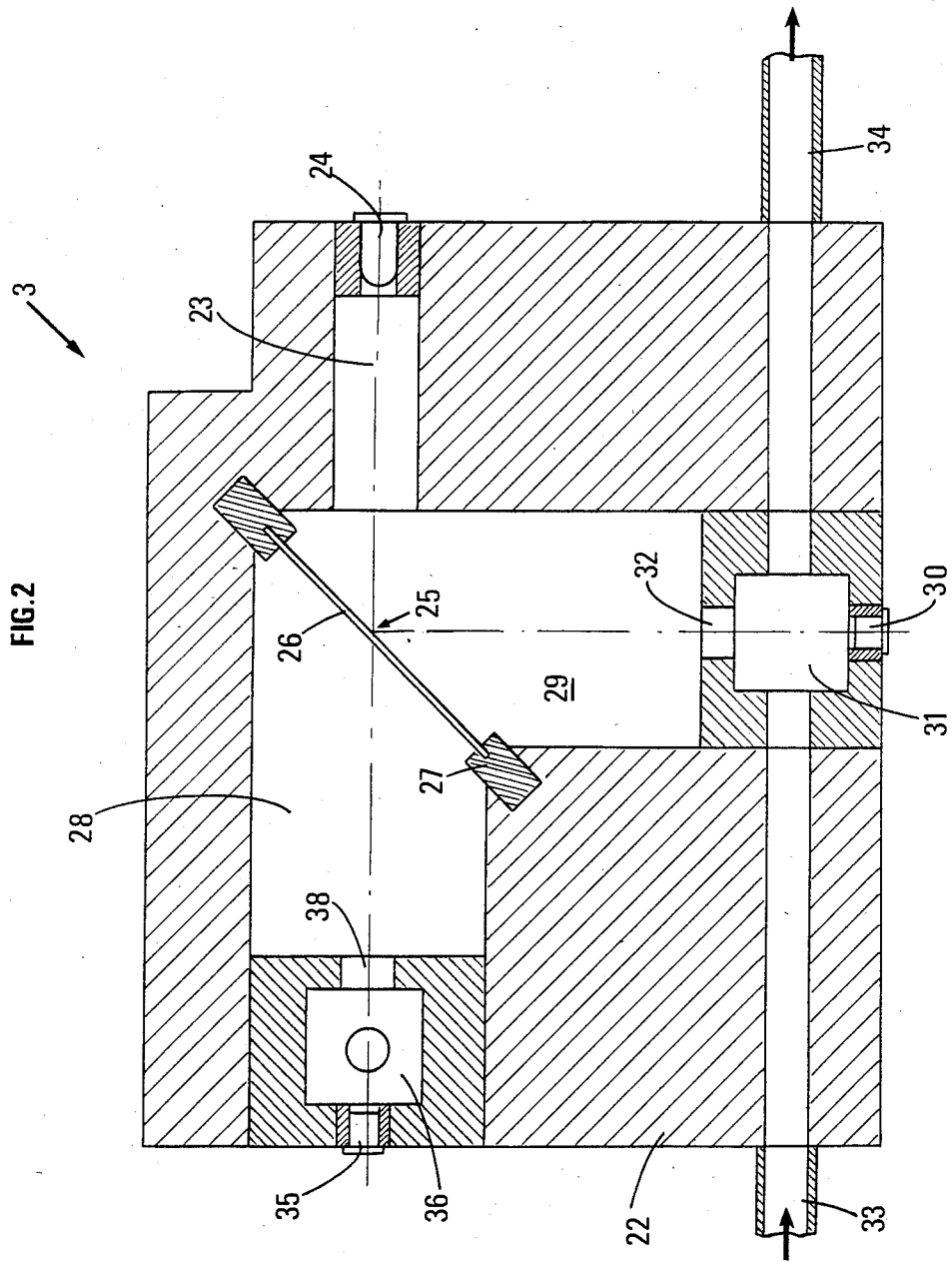
FIG. 2 illustrates one embodiment of the sensor for measuring the composition of the fuel mixture.

In FIG. 2 illustrating one embodiment of sensor 3 for determining the composition of the fuel mixture, reference 22 designates the body of this sensor, formed from a light alloy block. This block is pierced with a bore 23 in which is housed a light source 24 which may be formed by a light-emitting diode of the LEDME type 7124 from General Instrument emitting a light beam 25 in the infra-red range (average wave length 940 nanometers). This beam is divided into two parts by a semi-reflecting separating plate 26, with parallel faces, carried by a support 27 situated at the intersection of two other bores 28 and 29 in block 22. The axes of these two bores are perpendicular, the axis of bore 28 coinciding with that of bore 23.

A part of beam 25 is reflected towards a first photo meter such as a photo transistor 30 through a measuring cell 31. This measuring cell 31, having a window 32 made from a material which only weakly absorbs the emitted radiation, comprises input and output tubes, 33 and 34 respectively, connected to pipe 2 of the fuel feed circuit of the engine, so as to have passing therethrough the alcohol-petrol mixture supplying the engine. A filter 37 is placed in the input tube of the sensor (FIG. 3).

The other part of beam 25 passes without deflection through the separating plate 26 and reaches a second photometer such as a photo transistor 35 through a cell 36 having the window 38, and preferably similar to the measuring cell, but containing a reference liquid of known composition, for example pure methanol $CH_3OH$.

Still withing the scope of the present invention, this reference cell may be replaced by a simple filter having known absorption characteristics preferably substantially equivalent to those which the measuring cell would have if it were filled with an alcohol and petrol mixture whose composition were known.

Figure 3:
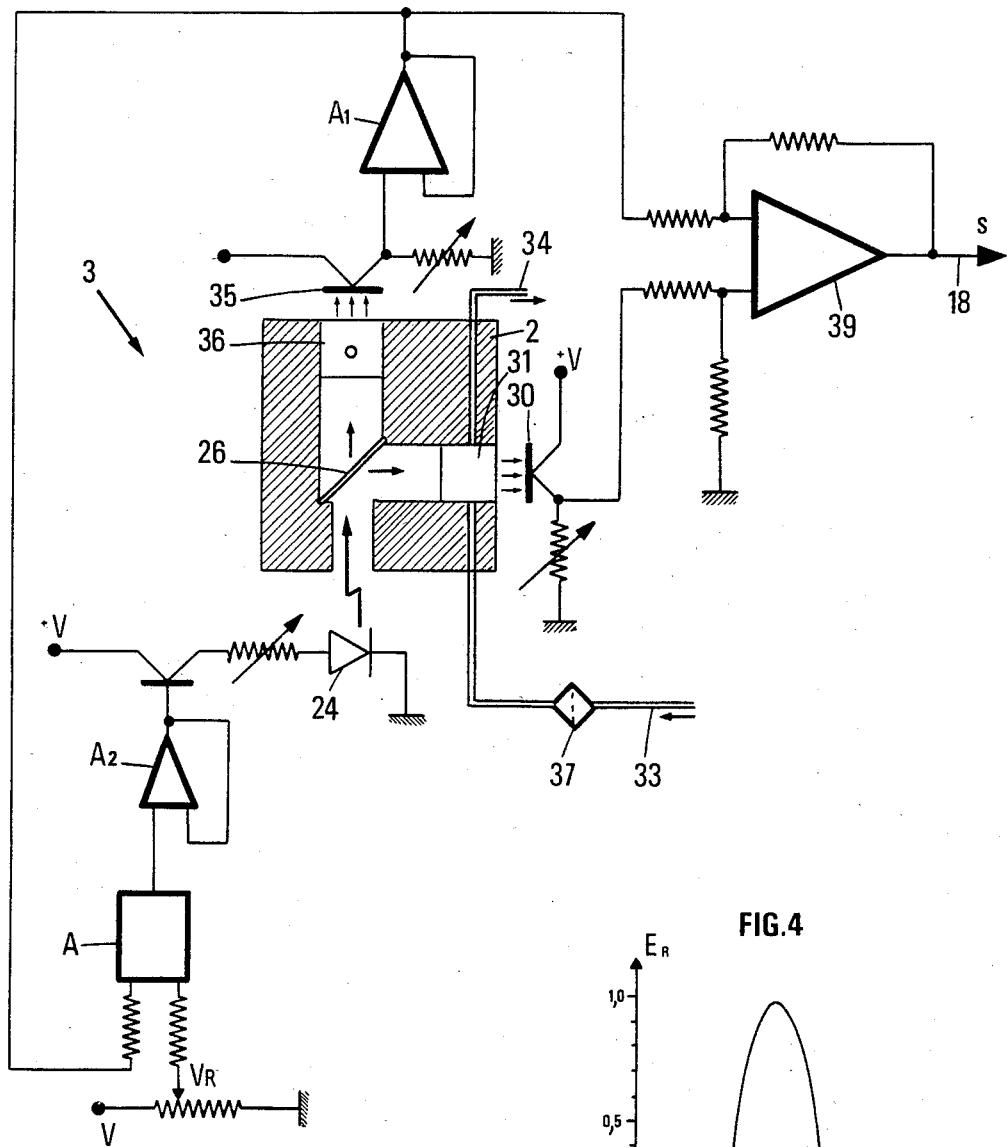
FIG. 3 shows schematically the electric circuits associated with the sensor.

The composition of the respective degrees of absorption of the radiation by the liquid flowing through the measuring cell 31 and by the liquid contained in the reference cell 36 may be provided by means of a differential amplifier 39 whose two inputs are connected respectively to the photo transistors 30 and 35 (FIG. 3).

The measurement signal S delivered by the differential amplifier 39 is transmitted to the automatic data processing means ADP through the conductor 18.

FIG. 3, in which the reference $+V$ designates an electric voltage source (For example 10 volts), shows moreover schematically how automatic regulation of the light flux produced by the emitting photo-diode 24 may be achieved to this end, an amplifier of the follower type $A_1$ is connected to the emitter of the reference photo transistor 35. The output signal of this follower, which is applied to one of two inputs of the differential amplifier 39, to transmitted to a first input of a servo system comprising an operational amplifier A whose second input terminal is brought to a reference electric voltage $V_R$. The output terminal of the operational amplifier $A_1$ is connected through a follower $A_2$ to the base of a transistor whose emitter is connected to the emitting diode 24.

This regulation system separates as follows: if the electric voltage delivered by the photo transistor 35 associated with the reference cell 36 decreases (because of ageing of the diode 24 or because of dirt in the window of the reference cell 36), the operational amplifier A controls, depending on the difference between this voltage and the reference voltage $V_R$, an increase in the supply voltage of the emitting diode 24 so as to re-establish at the desired level the light flux emitted by this diode.

Figure 4:
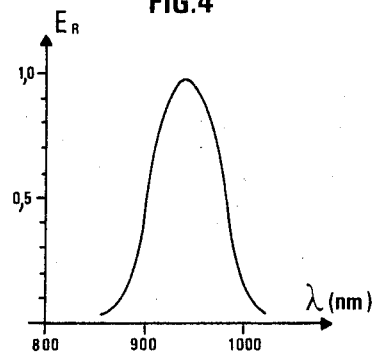
FIG. 4 shows the emission curve of a light emitting photo diode which may be used in the device of the invention.

FIG. 4 shows the characteristic emission curve of a photo-diode (photo-diode I.R.ME 7124) which may be used for the emitting diode 24 of sensor 3. In this Figure, the wave length $\lambda$ in nanometers is shown in abscissa, the relative emission $E_R$ being plotted as ordinates.

FIG. 5 shows the percentage of light transmission for different fuel mixture constituents as a function of the wave length $\lambda$ in nanometers.

The measurement signal S delivered by the differential amplifier 39 is proprotional to the difference of the input signals. The zero of this amplifier is adjusted when the two cells 31 and 36 both contain the reference liquid (CH$_3$OH) and the gain adjustment of this amplifier 39 for the full scale is effected when the measuring cell 31 contains pure petrol, the reference cell 36 still containing pure methanol.

FIG. 6 shows a calibration curve for a sensor such as the one illustrated in FIG. 3.

This curve gives the value of the measurement signal S transmitted to the automatic data processing means ADP as a function of the methanol percentage CH$_3$OH.

By way of example, for fuels formed from methanol-petrol mixtures, if $V_1$ designates the volume of mixture 1 with a density $D_1$ contained in the reservoir before replenishment effected at the service station and if $V_2$ designates the volume of mixture 2 delivered by the pump, $(A/F)_1$ and $(A/F)_2$ being the characteristic stoichiometric ratios of mixtures 1 and 2 respectively, the values $V_3$, $D_3$ and $(A/F)_3$ of the resulting mixture 3 obtained in the reservoir are related to the preceding ones by the volumetric relationships;

$$V_1 D_1 (A/F)_1 + V_2 D_2 (A/F)_2 = V_3 D_3 (A/F)_3 \quad (1)$$

with $$V_1 + V_2 \simeq V_3 \text{ (within 0.4\%)} \quad (2)$$

and $$(V_1 D_1 + V_2 D_2)/(V_1 + V_2) \simeq D_3 \quad (3)$$

The automatic data processing means ADP may be adapted to determine, after each replenishment, the values $(A/F)_3$, $V_3$ and $D_3$ of the resulting mixture 3 on the basis of the three above relationships (1), (2) and (3) from the initial values $(A/F)_1, V_1$ and $D_1$ and from the values $(A/F)_2$, $V_2$ and $D_2$ characterizing the replenishment effected.

Still within the scope of the present invention, a light beam separation means may be used other than a separating plate, this means being adapted to separate the incident light beam into at least two other beams. Such a means may, for example, be an optical fiber in the shape of a Y, or by periodically deflecting the incident beam for example by using an oscillating mirror or any other device of the same kind. Similarly, two different light sources may be used having preferably substantially identical characteristics, one of these sources emitting radiation towards the measuring cell and the other towards the reference cell.

The present invention may be applied to mixtures other than alcohol-petrol mixtures, particularly to a mixture containing at least one oxygenated product and petrol.

What is claimed is:

1. In a process for automatically adjusting operating parameters of a combustion engine fed with an alcohol-petrol mixture, a light beam is emitted through a mixture supplying the engine, the degree to which this beam is absorbed by the mixture is determined in a wave length band chosen in the wave length range of between 700 and 1700 namometers and an adjustment of the operating parameters of the engine is controlled as a function of the degree of absorption thus measured.

2. The process as claimed in claim 1, characterized in that the degree of absorption is determined for a wave length between 900 and 1000, nanometers.

3. The process as claimed in claim 1, characterized in that the degree of absorption is determined for a wave length between 1,450 and 1,600 nanometers.

4. The process as claimed in claim 1, wherein a second light beam is emitted through a reference liquid.

5. The process as claimed in claim 4, wherein said reference liquid comprises alcohol.

6. A device useable for automatically adjusting at least one operating parameter of a combustion unit such as an engine, supplied with a mixture containing petrol, such as an alcohol-petrol mixture, such as the air/fuel ratio of the supply, the ignition advance, the recycling rate of the unburnt gas, there is further provided a sensor comprising a light source, emitting a first light beam through a cell through which flows the mixture supplying said combustion unit and a means for measuring the degree to which this beam is absorbed by the mixture flowing through the cell for at least one wave length chosen in the wave length range of between 700 and 1700 nanometers, this measuring means delivering a signal as a function of the degree of absorption measured.

7. The device as claimed in claim 6, wherein said measuring means is connected to means for adjusting at the least one operating parameter of an engine, as a function of said signal delivered by said measuring means.

8. The device as claimed in claim 6, wherein said sensor comprises a first photometer receiving a part at least of the light beam emitted by the light source after this latter has passed through the measuring cell through which flows the mixture supplying said combustion unit and a second photometer receiving a part at least of the light beam emitted by the light source, after this latter has passed through a second reference cell.

9. The device as claimed in claim 8, wherein the reference cell is identical to the measuring cell and contains a reference liquid.

10. The device as claimed in claim 9, wherein said reference fluid is alcohol.

11. The device as claimed in claim 8, wherein there is further provided a plate for separating the light beam emitted by the light source.

12. The device as claimed in claim 8, further comprising a means for separating the incident light beam into at least two other beams.

13. In a device for automatically adjusting at least one operating parameter of a combustion unit such as an engine, supplied with a mixture containing petrol, such as an alcohol-petrol mixture, such as the air/fuel ratio of the supply, the ignition advance, the recycling rate of the unburned gas, there is further provided a sensor comprising a light source, emitting a first light beam through a cell through which flows the mixture supplying said combustion unit and a means for measuring the degree to which this beam is absorbed by the mixture flowing through the cell for at least one wave length chosen in the wave length range corresponding to the near infra-red, the measuring means delivering a signal as a function of the degree of absorption measured and being connected to means for adjusting the at least one operating parameter of the engine, as a function of said signal delivered by said measuring means, and wherein said sensor is disposed in series with a fuel pump in a supply pipe containing a fuel reservoir to the engine, said reservoir includes a fuel gauge adapted to a produce a signal translating an increase in volume of the fuel in the reservoir, and a by-pass valve towards a return pipe to the reservoir is disposed in a supply pipe and connected to means for controlling the by-pass, said control means being adapted to be activated during a given time interval on receiving a control signal delivered by the fuel gauge and related to an increase in the volume of fuel in the reservoir.

* * * * *